US012763363B2

(12) United States Patent
Zhao et al.

(10) Patent No.: US 12,763,363 B2
(45) Date of Patent: Oct. 13, 2026

(54) MULTIFUNCTIONALIZED THIOL CONDUCTOR COMPOUND AND METHOD FOR MAKING SAME

(71) Applicants: BLUE SOLUTIONS CANADA INC., Boucherville (CA); CAPACITOR SCIENCES INCORPORATED, Menlo Park, CA (US)

(72) Inventors: Qiujie Zhao, Menlo Park, CA (US); Siwei Liang, Menlo Park, CA (US); Jin Yang, Menlo Park, CA (US); Sarah Degras, Brossard (CA); Patrick Leblanc, Boucherville (CA)

(73) Assignee: BLUE SOLUTIONS CANADA INC., Boucherville (CA)

( * ) Notice: Subject to any disclaimer, the term of this patent is extended or adjusted under 35 U.S.C. 154(b) by 588 days.

(21) Appl. No.: 18/357,342

(22) Filed: Jul. 24, 2023

(65) Prior Publication Data

US 2024/0047745 A1 Feb. 8, 2024

Related U.S. Application Data

(60) Provisional application No. 63/394,098, filed on Aug. 1, 2022.

(51) Int. Cl.

| | |
|---|---|
| ***H01M 10/0565*** | (2010.01) |
| ***C07C 311/48*** | (2006.01) |
| ***H01M 10/0525*** | (2010.01) |

(52) U.S. Cl.

CPC ....... *H01M 10/0565* (2013.01); *C07C 311/48* (2013.01); *H01M 10/0525* (2013.01); *H01M 2300/0082* (2013.01)

(58) Field of Classification Search

CPC ......................... H01M 10/0565; C07C 311/48

See application file for complete search history.

(56) References Cited

U.S. PATENT DOCUMENTS

| | | | |
|---|---|---|---|
| 2019/0088997 A1 | 3/2019 | Bouchet et al. |
| 2021/0001007 A1 | 1/2021 | Pelling et al. |

FOREIGN PATENT DOCUMENTS

| | | |
|---|---|---|
| CN | 109888289 A | 6/2019 |
| CN | 111769321 A | 10/2020 |

OTHER PUBLICATIONS

Zhang et al., Artificial single-ion conducting polymer solid electrolyte interphase layer toward highly stable lithium anode, ACS Applied Energy Materials, 4(1), pp. 862-869, Jan. 12, 2021.

Kadulkar et al., The importance of morphology on ion transport in single-ion, comb-branched copolymer electrolytes: experiments and simulations, Macromolecules, 56(7), pp. 2790-2800, Mar. 30, 2023.

Chouirfa et al., Single-ion nano-features formed by a Li-containing block copolymer synthesized via PISA, Polymer Chemistry, 14(25), pp. 2971-2978, Jun. 1, 2023.

International Search Reprot and Written Opinion issued in co-pending International application No. PCT/CA2023/050985 on Oct. 24, 2023.

*Primary Examiner* — Kregg T Brooks

(74) *Attorney, Agent, or Firm* — BCF LLP

(57) ABSTRACT

The present technology relates to multifunctionalized thiol conductor compounds which can be grafted onto polymers, and methods for making same. In certain embodiments, the compounds of the present technology can be grafted onto polymers having low Tg to synthesize single-ion conducting polymer electrolytes having improved conductivity. The multifunctionalized thiol conductor compounds of the present technology generally comprise more than one sulfonamide anion covalently attached to a substitutable core (A) via a sulphide bond, a thiol functional group and optionally a hydrocarbon side chain (L) attached to the substitutable core (A).

23 Claims, 2 Drawing Sheets

MULTIFUNCTIONALIZED THIOL CONDUCTOR COMPOUND AND METHOD FOR MAKING SAME

CROSS-REFERENCE TO RELATED APPLICATION

This application claims the benefit of and priority to U.S. provisional patent application No. 63/394,098, filed on Aug. 1, 2022; the content of which is herein incorporated in entirety by reference.

TECHNICAL FIELD

The present technology generally relates to single ion polymer electrolytes, and in particular to multifunctionalized thiol conductor compounds and methods for making same.

BACKGROUND

A lithium battery using a lithium metal as a negative electrode has excellent energy density. However, with repeated cycles, such a battery can be subject to dendrite growth on the surface of the lithium metal electrode when recharging the battery, as the lithium ions are unevenly re-plated on the surface of the lithium metal electrode. To minimize the effect of the morphological evolution of the surface of the lithium metal anode including dendrite growth, a lithium metal battery typically uses a pressure system and a solid polymer electrolyte adapted to resist the pressure applied thereto as described in U.S. Pat. No. 6,007,935 (incorporated herein by reference). Over numerous cycles, dendrites on the surface of the lithium metal anode, however, may still grow to penetrate the solid polymer electrolyte, and eventually cause 'soft' short circuits between the negative electrode and the positive electrode, resulting in decreasing or poor performance of the battery. Therefore, the growth of dendrites may still deteriorate the cycling characteristics of the battery and constitutes a major limitation with respect to the optimization of the performance of lithium batteries having a metallic lithium anode.

Various types of solid polymer electrolytes adapted for use with lithium metal electrodes have been developed since the late 1970s to overcome this issue but have been found to lack in conductivity and/or mechanical properties. Single-ion conducting polymer electrolytes (SIPE) have, however, emerged as promising candidates, as the transference number of lithium cation approaches unity, and therefore prevents the formation of concentration gradients across the electrolyte, and dendrite formation as a result.

Currently, existing routes of synthesis of single-ion polymer electrolytes include synthesis of poly(ethylene oxide) methacrylate lithium sulfonyl(trifluoromethylsulfonyl) imide) (PEOMA-TFSI-$Li^+$) monomers via a copper-catalyzed alkyne-azide "click chemistry" cycloaddition as illustrated in FIG. 1.

The synthesis of azide-clicked PEOMA-TFSI-Lit is however complex and not suitable for scale-up production for at least the following reasons: (1) azide and alkyne functional groups must be installed on the precursors; (2) the intermediate molecules are expensive to make and not commercially available; (3)alkali azide salts, such as $LiN_3$ and $NaN_3$, are dangerous and hard to handle in large quantity, preventing the scale up of the precursors; (4) the final polymer is a PEO based polymer, which is not suitable for high voltage applications; and (5) the chemistry is not versatile in terms of functional group availability as commercial polymers with internal triple bonds are rare.

Alternatively, existing functionalized LiTFSI monomers, such as single TFSI thiol compounds, offer a limited increase in ion concentration once grafted onto polymers, especially when C═C bonds are scarce or not easily accessible in the polymer being grafted.

Therefore, there is a need for alternative or improved functionalized TFSI monomers which overcome or reduce at least some of the above-described problems.

SUMMARY OF THE TECHNOLOGY

The inventors of the present technology have recently discovered novel routes of synthesis of single-ion polymer electrolytes which include the synthesis of LiTFSI monomers with reduced cost and high atom economy (i.e., produce minimal reactant waste) by virtue of, inter alia, comprising a single step and bypassing the synthesis of nitrogen-based organic cation intermediates. These novel synthesis routes can be applied to make SIPEs with styrene, acrylate or methacrylate backbones. However, the resulting homopolymers derived from such LiTFSI monomers have high glass transition temperatures (Tg) and low conductivity at room temperature which hinder their performance as electrolytes and ultimately the performance of the battery. Moreover, such LiTFSI monomers do not comprise functional groups suitable for grafting onto polymers with low Tgs to help alleviate those defects.

From a broad aspect, the present technology relates to multifunctionalized thiol conductor compounds. In certain embodiments, the multifunctionalized thiol conductor compound comprises one or more thiol functional groups which allow the multifunctionalized thiol conductor compound to be easily grafted onto polymers, optionally having low Tg, in order to synthesize single-ion conducting polymer electrolytes (SIPE) with improved conductivity.

From one aspect, there is provided a multifunctionalized thiol conductor compound having formula I:

(formula I)

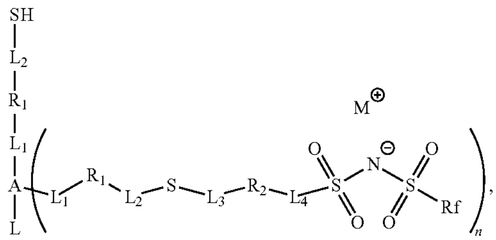

wherein:

A is a substitutable core;

L is absent or present and when present is a n-alkyl group, a fluorinated alkyl group, a branched alkyl group, an ethylene oxide group, a fluorinated ethylene oxide group, a cycloalkyl group, a fluorinated cycloalkyl group, a phenyl group, or a fluorinated phenyl group;

$R_f$ is F, $CF_3$, $CF_2CF_3$, $(CH_2)_nCF_3$ wherein n is ≥1, $C_6F_5$, a branched $C_3$-$C_4$ fluoroalkyl group, —$(CF_2CF_2O)_m$—$CF_2CF_3$ wherein m=1, 2 or 3, —$(CF_2O)$ p/$(CF_2CF_2O)$ q-$CF_2CF_3$ wherein 1≤p≤10, 1≤q≤10, and the $(CF_2O)$ and $(CF_2CF_2O)$ units are randomly copolymerized, or an aryl substituted with at least one fluorine, and at least one electron-withdrawing group;

$M^+$ is a monovalent cation;

$L_1$ is absent or present and when present is a n-alkyl group, a fluorinated alkyl group, a branched alkyl group, an ethylene oxide group, a fluorinated ethylene oxide group, a cycloalkyl group, a fluorinated cycloalkyl group, a phenyl group, or a fluorinated phenyl group;

$L_2$ is absent or present and when present is a n-alkyl group, a fluorinated alkyl group, a branched alkyl group, an ethylene oxide group, a fluorinated ethylene oxide group, a cycloalkyl group, a fluorinated cycloalkyl group, a phenyl group, or a fluorinated phenyl group;

$L_3$ is absent or present and when present is a n-alkyl group, a fluorinated alkyl group, a branched alkyl group, an ethylene oxide group, a fluorinated ethylene oxide group, a cycloalkyl group, a fluorinated cycloalkyl group, a phenyl group, or a fluorinated phenyl group;

$L_4$ is absent or present and when present is a n-alkyl group, a fluorinated alkyl group, a branched alkyl group, an ethylene oxide group, a fluorinated ethylene oxide group, a cycloalkyl group, a fluorinated cycloalkyl group, a phenyl group, or a fluorinated phenyl group;

$R_1$ is absent or present and when present is an ether, a thioether, an ester, an amide, a carbamic acid derivative, urea, a secondary amine, or a tertiary amine;

$R_2$ is absent or present and when present is an ether, a thioether, an ester, an amide, a carbamic acid derivative, urea, a secondary amine, or a tertiary amine; and $$n > 1.$$

From another aspect, there is provided a method for the synthesis of the multifunctionalized thiol conductor compound of the present technology, the method comprising reacting a multifunctional thiol compound with a lithium bis(trifluoromethanesulfonyl)imide (LiTFSI)-monomer having a C═C in its backbone.

From another aspect, there is provided a single-ion conducting polymer electrolyte comprising the multifunctionalized thiol conductor compound of the present technology.

From another aspect, there is provided a single-ion conducting polymer cathode comprising the multifunctionalized thiol conductor compound of the present technology.

From another aspect, there is provided a single-ion conducting polymer anode comprising the multifunctionalized thiol conductor compound of the present technology.

From another aspect, there is provided a solid-state battery comprising a positive electrode, a negative electrode and the single-ion conducting polymer electrolyte of the present technology.

From another aspect, there is provided a solid-state battery comprising the single-ion conducting polymer cathode of the present technology, a negative electrode and an electrolyte.

From another aspect, there is provided a solid-state battery comprising a positive electrode, the single-ion conducting polymer anode of the present technology, and an electrolyte.

From another aspect, the multifunctionalized thiol conductor compound of the present technology can be grafted onto different polymers.

From another aspect, the multifunctionalized thiol conductor compound of the present technology can increase ion concentration on the polymer onto which it is grafted compared to single thiol TFSI compounds, when the grafting density is the same. This is particularly useful when the available C═C bonds are scarce or not easily accessible on the polymer.

From another aspect, the methods of the present technology are facile and do not require heating.

BRIEF DESCRIPTION OF THE DRAWINGS

Reference will now be made to the accompanying drawings.

DETAILED DESCRIPTION

Definition

Figure 1:
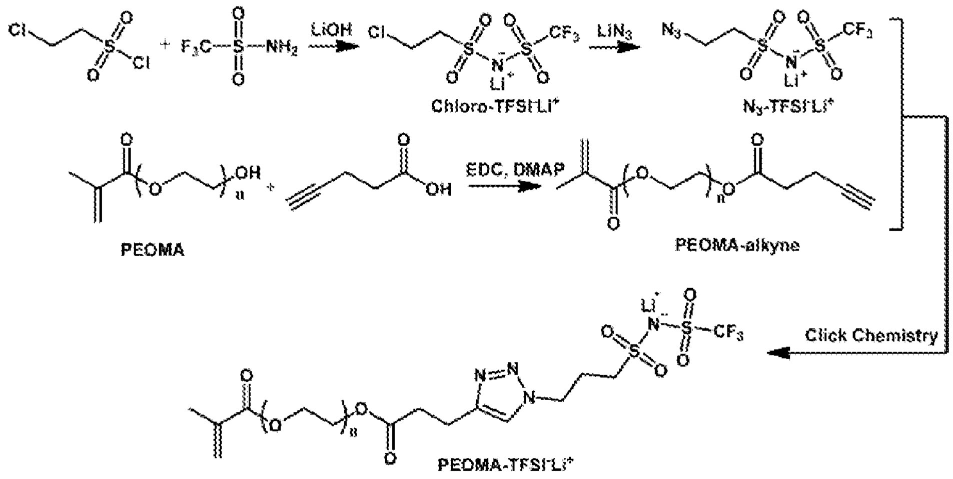
FIG. 1 PRIOR ART
FIG. 1 illustrates an existing synthesis route for poly (ethylene oxide) methacrylate lithium sulfonyl(trifluoromethylsulfonyl)imide) (PEOMA-TFSI-$Li^+$) according to Sipei Li et al., ACS Energy Lett. 2018, 3, 1, 20-27 (incorporated herein by reference) using an azide-alkyne click chemistry.

The use of "including", "comprising", or "having", "containing", "involving" and variations thereof herein, is meant to encompass the items listed thereafter as well as, optionally, additional items.

It must be noted that, as used in this specification and the appended claims, the singular form "a", "an" and "the" include plural referents unless the context clearly dictates otherwise.

As used herein, the term "and/or" is to be taken as specific disclosure of each of the two specified features or components with or without the other. For example, "A and/or B" is to be taken as specific disclosure of each of (i) A, (ii) B and (iii) A and B, just as if each is set out individually herein.

As used herein, the expression "single-ion conducting polymer" is a polymer comprising an immobile anion as part of its chemical structure. As used herein, the expression immobile anion refers to anions which are not displaced during the charge/discharge cycles of the battery.

As used herein, the expression "multifunctional thiol compound" refers to a thiol compound having more than two thiol groups in one molecule. Such multifunctional thiol compounds can therefore react with more than one LiTFSI-monomer having a C═C in their backbone in the methods of the present technology and have more than one LiTFSI-monomer attached thereto.

As used herein, the expressions "click chemistry" or "click reaction" refers to a reaction which is simple; has a high efficiency, a high yield; and generates byproducts which are stereospecific and can be easily removed. Moreover, such reactions can be conducted in easily removable or benign solvents. Click chemistry was conceptualized by Sharpless et al., Angew. Chem. Int. Ed. 2001, 40, 2004-2021, incorporated herein by reference.

As used herein, the term "about" in the context of a given value or range refers to a value or range that is within 20%, preferably within 10%, and more preferably within 5% of the given value or range.

The present disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting.

Broadly, the present technology relates to multifunctionalized thiol conductor compounds which can be grafted onto polymers, such as commercially available polymers, including, but not limited to, polyethylene oxide (PEO), polyvinylidene fluoride (PVDF), and poly(acrylonitrile-co-butadiene). In some instances, the grafting reaction of the multifunctionalized thiol conductors with such polymers comprises a thiol-ene "click" reaction which can be used to generate single-ion conducting polymer electrolytes (SIPE) having low Tg. As such, the SIPE comprising the multifunctionalized thiol conductors of the present technology have higher conductivity than the SIPEs obtained by the polymerization of LITFSI-containing monomers having styrene, acrylate or methacrylate backbones.

In certain embodiments, the multifunctionalized thiol conductor compound of the present technology comprises more than one sulfonamide anion covalently attached to a substitutable core (A) via a sulphide bond. The multifunctionalized thiol conductor compound further comprises a thiol functional group and optionally a hydrocarbon side chain (L) attached to the substitutable core (A). The multifunctionalized thiol conductor compound may further comprise between 0 and 4 hydrocarbon chains as linkers ($L_1$-$L_4$) and between 0 and 2 functional groups ($R_1$ and $R_2$); which connect the thiol group and/or the sulfonamide anions to the substitutable core (A).

In some embodiments, the multifunctionalized thiol conductor compound has formula I:

(formula I)

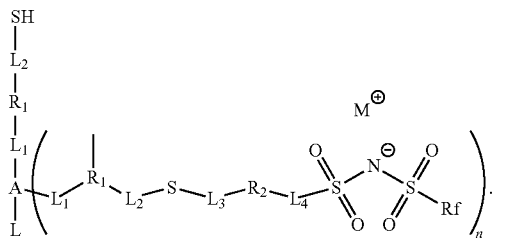

A is a substitutable core able to accept at least n+1 substituents, wherein n is an integer representing the number of sulfonamide anions to be attached to A. In some embodiments, A is able to accept n+1 substituents. In other embodiments, A is able to accept n+2 substituents.

In certain embodiments, n>1. In some embodiments, n is 2, 3, or 5. In other embodiments, n is 2. In yet other embodiments, n is 3. In further embodiments, n is 5.

In certain embodiments, the substitutable core A is a boron atom, an aluminum atom, a carbon atom, or a silicon atom. In some embodiments, A is a carbon. In other embodiments, A is

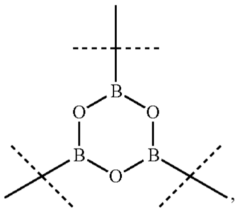, 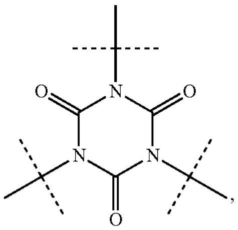, or

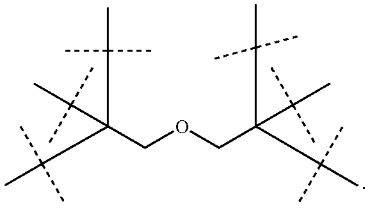.

In certain embodiments, depending on the substitutability of A and the value of n (i.e., sulfonamide anions attached to A), L may be absent or present. When present, L may be a n-alkyl group, a fluorinated alkyl group, a branched alkyl group, an ethylene oxide group, a fluorinated ethylene oxide group, a cycloalkyl group, a fluorinated cycloalkyl group, a phenyl group, or a fluorinated phenyl group. In some embodiments, L is absent. In other embodiments, L is a n-alkyl group and n is 1, 2, 3, 4, 5 or 6. In further embodiments, L is —$CH_2CH_3$.

In certain embodiments, $R_f$ is F, $CF_3$, $CF_2CF_3$, $(CH_2)_nCF_3$ wherein n is ≥1, $C_6F_5$, a branched $C_3$-$C_4$ fluoroalkyl group, a linear perfluorethylether group, such as—$(CF_2CF_2O)_m$—$CF_2CF_3$ wherein m=1, 2 or 3, —$(CF_2O)$ p/$(CF_2CF_2O)$ q-$CF_2CF_3$ wherein 1≤p≤10, 1≤q≤10, and the $(CF_2O)$ and $(CF_2CF_2O)$ units are randomly copolymerized, or an aryl substituted with at least one fluorine and at least one electron-withdrawing group. In some embodiments, the branched $C_3$-$C_4$ fluoroalkyl group comprises —CF—$(CF_3)_2$, —$CF(CF_3)$—$CF_2$—$CF_3$, and $CF_2$—CF—$(CF_3)_2$. In other embodiments, the electron-withdrawing group is —CN, —$NO_2$, —$CF_3$, or —$SO_2CF_3$. In further embodiments, the aryl compound substituted with the at least one fluorine and the at least one electron-withdrawing group is —$C_6F_4$—$CF_3$, or —$C_6F_4$—$SO_2CF_3$. In yet further embodiments, $R_f$ is $CF_3$.

$M^+$ in the multifunctionalized thiol conductor compound of the present technology is a monovalent cation. In some embodiments, the monovalent cation is an alkali metal cation. In other embodiments, the alkali metal cation is $H^+$, $K^+$, $Na^+$, $Li^+$, $Rb^+$, or $Cs^+$. In yet other embodiments, the alkali metal cation is $Li^+$.

As discussed above, $L_1$, $L_2$, $L_3$ and $L_4$ in the multifunctionalized thiol conductor compounds of the present technology are linkers, which connect the thiol group and/or the sulfonamide anions to the substitutable core (A).

In certain embodiments, $L_1$ is absent. In other embodiments, $L_1$ is present. When present, $L_1$ may be a n-alkyl group, a fluorinated alkyl group, a branched alkyl group, an ethylene oxide group, a fluorinated ethylene oxide group, a cycloalkyl group, a fluorinated cycloalkyl group, a phenyl group, or a fluorinated phenyl group. In yet other embodiments, $L_1$ is a n-alkyl group and n is 1, 2, 3, 4, 5 or 6. In further embodiments, $L_1$ is —$CH_2$—.

$L_2$ may also be absent or present. When present, $L_2$ may be a n-alkyl group, a fluorinated alkyl group, a branched alkyl group, an ethylene oxide group, a fluorinated ethylene oxide group, a cycloalkyl group, a fluorinated cycloalkyl group, a phenyl group, or a fluorinated phenyl group. In some embodiments, $L_2$ is absent.

$L_3$ may also be absent or present. When present, $L_3$ may be a n-alkyl group, a fluorinated alkyl group, a branched alkyl group, an ethylene oxide group, a fluorinated ethylene oxide group, a cycloalkyl group, a fluorinated cycloalkyl group, a phenyl group, or a fluorinated phenyl group. In some embodiments, $L_3$ is a n-alkyl group and n is 2, 3, 4, 5 or 6. In other embodiments, $L_3$ is $(CH_2)_2$. In some embodiments, $L_3$ is absent.

$L_4$ may also be absent or present. When present, $L_4$ may be a n-alkyl group, a fluorinated alkyl group, a branched alkyl group, an ethylene oxide group, a fluorinated ethylene oxide group, a cycloalkyl group, a fluorinated cycloalkyl group, a phenyl group, or a fluorinated phenyl group. In some embodiments, $L_4$ is absent.

$R_1$ and $R_2$ in the multifunctionalized thiol conductor compound are functional groups which may be either absent or present. When present, $R_1$ and $R_2$ may each independently be an ether, a thioether, an ester, an amide, a carbamic acid derivative, urea, a secondary amine, or a tertiary amine. In some embodiments, $R_1$ is an ester. In other embodiments $R_2$ is an ester. In yet other embodiments, $R_1$ and $R_2$ are both esters.

In one embodiment, $R_f$ is $CF_3$; $M^+$ is $Li^+$, L, $L_1$, and $L_3$ are each a n-alkyl group wherein n is 2, 3, 4, 5 or 6, $R_1$ is an ester; and $R_2$ is an ester. In another embodiment, $R_f$ is $CF_3$; $M^+$ is $Li^+$, L is —$CH_2CH_3$; $L_1$is —$CH_2$—; $L_3$ is $(CH_2)_2$; $L_2$ is absent; $L_4$ is absent; $R_1$ is an ester; and $R_2$ is an ester.

In certain embodiments, the multifunctionalized thiol conductor compound has formula II:

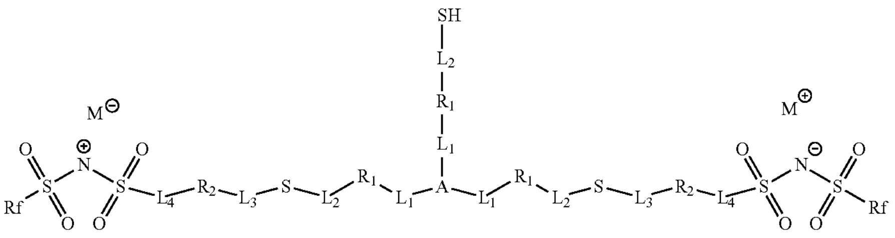

(formula II)

wherein $R_f$, $M^+$, $L_1$, $L_2$, $L_3$, $L_4$, $R_1$ and $R_2$ have the same definition as in formula I, A is a boron atom, an aluminum atom,

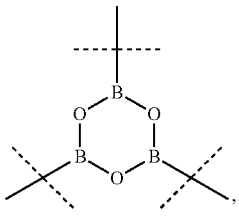

, or

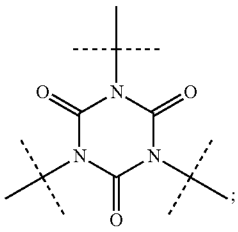

;

and

L is absent.

In certain implementations of these embodiments, A is a boron atom or an aluminum atom. In other implementations, A is a boron or aluminum atom; $R_f$ is $CF_3$; $M^+$ is Lit; $L_1$, and $L_3$ are each a n-alkyl group wherein n is 2, 3, 4, 5 or 6; $R_1$ is an ester; and $R_2$ is an ester. In other implementations, $R_f$ is $CF_3$; $M^+$ is $Li^+$, $L_1$ is $—CH_2—$; $L_3$ is $(CH_2)_2$; $L_2$ is absent; $L_4$ is absent; $R_1$ is an ester; and $R_2$ is an ester.

In certain embodiments, the multifunctionalized thiol conductor compound has formula II:

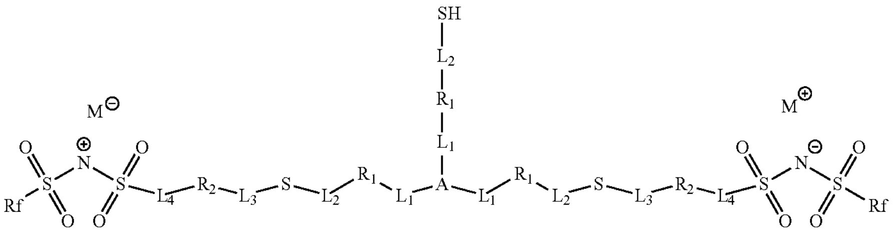

(formula II)

wherein $R_f$, $M^+$, L, $L_1$, $L_2$, $L_3$, $L_4$, $R_1$ and $R_2$ have the same definition as in formula I, A is a silicon or carbon atom, and L is present.

In certain implementations of these embodiments, A is carbon. In other implementations, L is a n-alkyl group and n is 1, 2, 3, 4, 5 or 6.

In yet other implementations, A is carbon; L is a n-alkyl group and n is 1, 2, 3, 4, 5 or 6; $R_f$ is $CF_3$; $M^+$ is $Li^+$; $L_1$, and $L_3$ are each a n-alkyl group wherein n is 2, 3, 4, 5 or 6, $R_1$ is an ester; and $R_2$ is an ester.

In further implementations, A is carbon; L is $—CH_2CH_3$; $R_f$ is $CF_3$; $M^+$ is $Li^+$; $L_1$ is $—CH_2—$; $L_3$ is $(CH_2)_2$; $L_2$ is absent, $L_4$ is absent; $R_1$ is an ester; and $R_2$ is an ester.

In certain embodiments, the multifunctionalized thiol conductor compound has formula III:

(formula III)

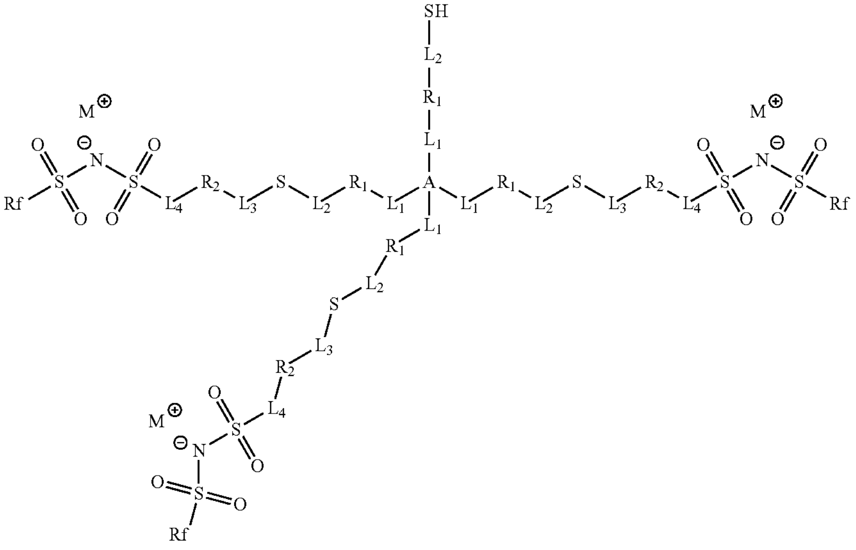

wherein $R_f$, $M^+$, $L_1$, $L_2$, $L_3$, $L_4$, $R_1$ and $R_2$ have the same definition as in formula I; A is a carbon atom or a silicon atom; and L is absent.

In certain implementations of these embodiments, A is carbon. In other implementations, A is carbon; $R_f$ is $CF_3$; Mis Lit; $L_1$ and $L_3$ are each a n-alkyl group wherein n is 2, 3, 4, 5 or 6, $R_1$ is an ester; and $R_2$ is an ester. In yet other implementations, A is carbon; $R_f$ is $CF_3$; $M^+$ is Lit; $L_1$ is $—CH_2—$; $L_2$ is absent; $L_3$ is $(CH_2)_2$; $L_4$ is absent; $R_1$ is an ester; and $R_2$ is an ester.

In certain embodiments, the multifunctionalized thiol conductor compound of has formula IV:

(formula IV)

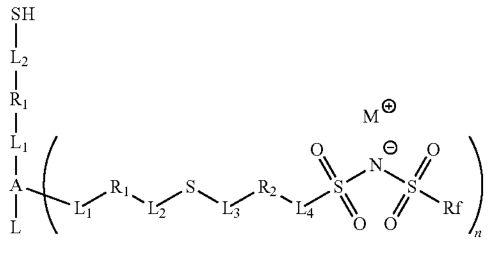

wherein $R_f$, $M^+$, $L_1$, $L_2$, $L_3$, $L_4$, $R_1$ and $R_2$ have the same definition as in formula I; A is a dipentaerythritol core

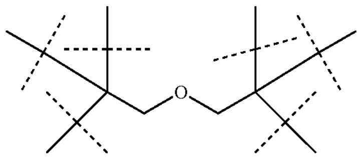

;

L is absent; and n=5.

In certain implementations of these embodiments, $R_f$ is $CF_3$; $M^+$ is Lit; $L_1$ and $L_3$ are each a n-alkyl group wherein n is 2, 3, 4, 5 or 6, $R_1$ is an ester; and $R_2$ is an ester.

In other implementations, $R_f$ is $CF_3$; $M^+$ is Lit; $L_1$ is $—CH_2—$; $L_2$ is absent; $L_3$ is $(CH_2)_2$; $L_4$ is absent $R_1$ is an ester; and $R_2$ is an ester.

In certain embodiments, the multifunctionalized thiol conductor compound has formula V or formula VI:

(formula V)

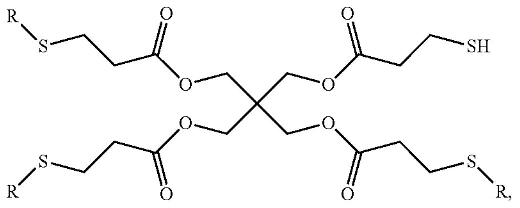

or

-continued (formula VI)

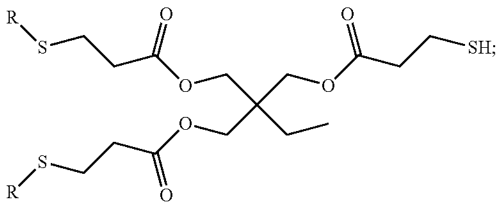

wherein R is

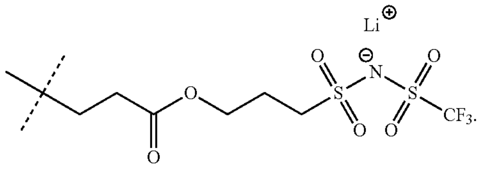

In other embodiments, the multifunctionalized thiol conductor compound has formula V. In yet other embodiments, the multifunctionalized thiol conductor compound has formula VI.

From another aspect, the present technology relates to methods of synthesis of the multifunctionalized thiol conductor compounds disclosed herein. In certain embodiments, the methods of the present technology comprise reacting a multifunctional thiol compound with a lithium bis(trifluoromethanesulfonyl)imide (LiTFSI)-monomer having a C═C in its backbone. Advantageously, the methods of the present technology comprise a single step. Moreover, direct addition of a multifunctional thiol compound on the LiTFSI-monomers in the methods of the present technology provide an easier route of synthesis than thiol functionalized LiTFSI-monomers with the thiol directly linked to the LiTFSI via an alkyl chain.

In certain embodiments, the reaction of the multifunctional thiol compound with the LiTFSI-monomer having the C═C in its backbone is a thiol-ene "click" reaction. Advantageously, thiol-ene click reactions are simple and highly efficient. Such reactions also allow the creation of a large variety of new polymer structures while enabling great spatial and temporal control of the materials.

In certain embodiments, the C═C in the LiTFSI-monomer is at one end of the molecule. In some embodiments, the C═C is at one end of the molecule and the sulfonamide anion is at the other (opposite) end of the LiTFSI-monomer. In other embodiments, the LiTFSI-monomer has the following formula VII, formula VIII, formula IX, formula X, or formula XI:

(formula VII)

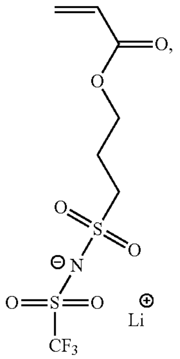

(formula VIII)

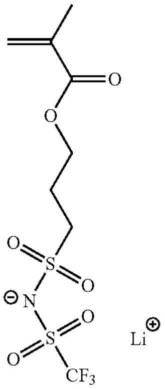

, (formula IX)

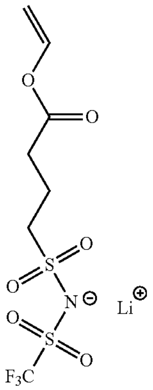

, (formula X)

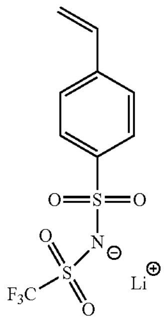

, or

-continued (formula XI)

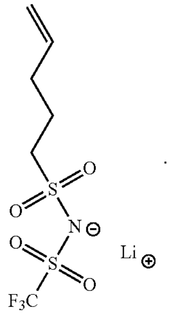

In certain embodiments, the multifunctional thiol compound is Pentaerythritol tetrakis(3-mercaptopropionate), Trimethylolpropane tris(3-mercaptopropionate), Tris [(3-mercaptopropionyloxy)-ethyl]-isocyanurate, and Dipentaerythritol hexakis (3-mercaptopropionate). In some embodiments, the thiol compound is Trimethylolpropane tris(3-mercaptopropionate). In other embodiments, the thiol compound is Pentaerythritol tetrakis(3-mercaptopropionate).

In some embodiments, the method comprises reacting an excess amount of the thiol compound with the LiTFSI-monomer. In other embodiments, the method comprises reacting about 1 to about 4 equivalent of the thiol compound with the LiTFSI-monomer. In yet other embodiments, the method comprises reacting about 1 to about 2 equivalent, or about 1 to about 3 equivalent of the multifunctional thiol compound with the LiTFSI-monomer.

In certain embodiments, the methods of the present technology comprise reacting the multifunctional thiol compound and the LiTFSI-monomer in bulk (i.e., without solvent). Such embodiments are plausible when the reactants are miscible in one another. In other embodiments, the methods of the present technology comprise reacting the multifunctional thiol compound and the LiTFSI-monomer in a solvent. In some embodiments, the solvent is water, methanol, ethanol, isopropanol, anhydrous methyl cyanide (MeCN), tetrahydrofuran (THF), acetone, dimethylformamide (DMF), or dimethyl sulfoxide (DMSO). In other embodiments, the multifunctional thiol compound and the LiTFSI-monomer are reacted in THF.

In certain embodiments, reacting the multifunctional thiol compound and the LiTFSI-monomer comprises dissolving the multifunctional thiol compound and the LiTFSI-monomer together in a solvent. In other embodiments, reacting the multifunctional thiol compound and the LiTFSI-monomer comprises dissolving the multifunctional thiol compound in a first solvent, dissolving the LiTFSI-monomer in a second solvent and adding the dissolved LiTFSI-monomer in the second solvent to the multifunctional thiol compound dissolved in the first solvent. In some embodiments, the first solvent and the second solvent are the same solvents. In other embodiments, the first solvent and the second solvent are different solvents. In such embodiments, the two different solvents are miscible in one another. The first solvent and second solvent may be any of the solvents disclosed above.

In certain embodiments, the methods of the present technology do not require a heating step. Specifically, in certain embodiments, the methods of the present technology comprise reacting the multifunctional thiol compound and the LiTFSI-monomer at a temperature of between about 15° C. and about 30° C. In other embodiments, the method comprises reacting the multifunctional thiol compound and the LiTFSI-monomer at a temperature of about 15° C., about 20° C., about 25° C. (room temperature (RT)), or about 30° C. In yet other embodiments, the method comprises reacting the multifunctional thiol compound and the LiTFSI-monomer at a temperature of about 25° C. (RT).

In certain embodiments, the methods of the present technology comprise adding a catalyst to the reaction of the multifunctional thiol compound and the LiTFSI-monomer. As used herein, the term "catalyst" refers to a substance that can be added to a reaction to increase the reaction rate without getting consumed in the process. In certain embodiments, the catalyst is triethylamine (Et3N), diethylamine, di-n-propylamine, a $C_2$-$C_6$ primary amine, N,N,N',N'-Tetramethyl-1,8-naphthalenediamine, 1,8-diazabicyclo [5.4.0] undec-7-ene (DBU), 1,5-diazabicyclo [4.3.0]non-5-ene (DBN), tripropylphosphine, dimethylphenylphosphine diphenylmethylphosphine, or triphenylphosphine.

In other embodiments, the catalyst is added at an amount of between about 0.05 mol % and about 30 mol %.

In further embodiments, the methods of the present technology comprise adding a free radical initiator to the reaction of the multifunctional thiol compound and the LiTFSI-monomer. As used herein, the expression "free radical initiator" refers to substances that can produce free radical species under mild conditions and promote radical reactions. As used herein the expression "free radical species" refers to an uncharged molecule, typically highly reactive and short-lived, having an unpaired valence electron. In the synthesis of the multifunctionalized thiol conductor compound, a free radical initiator may be used to generate a thiol free radical from the multifunctional thiol compound and/or to complete the reaction between the multifunctional thiol compound and the LiTFSI-monomer. In some embodiments, the free radical initiator is a thermal activated free radical initiator. In other embodiments, the free radical initiator is a photochemically activated free radical initiator. In further embodiments, the free radical initiator is Azobisisobutyronitrile (AIBN), Benzyl peroxide, 4,4'-Azobis(4-cyanovaleric acid) (ACVA), 2,2-Dimethoxy-2-phenylacetophenone (DMPA, Irgacure 651), 2-Hydroxy-2-methylpropiophenone (Irgacure 1173), or 2-Hydroxy-4'-(2-hydroxyethoxy)-2-methylpropiophenone (Irgacure 2959). In yet further embodiments, the free radical initiator is DMPA.

In further embodiments, the free radical initiator is added at an amount of between about 0.01 mol % and about 5.0 mol %, between about 0.01 mol % and about 2.0 mol %, between about 0.01 mol % and about 1.0 mol %, between about 0.01 mol % and about 0.5 mol %, between about 0.01 mol % and about 0.25 mol %, between about 0.01 mol % and about 0.1 mol %, or between about 0.01 mol % and about 0.05 mol %.

In certain embodiments, the free radical initiator is photochemically activated by UV light. In some embodiments, the UV light has a wavelength of between about 250 nm and about 450 nm, between about 300 nm and about 400 nm, or about 365 nm. In further embodiments, the free radical initiator is photochemically activated for a period of between about 1 minute to about 2 hours, between about 5 minutes to about 1 hour, between about 10 minutes to about 40 minutes, between about 10 minutes and about 50 minutes, between about 15 minutes and about 45 minutes, or about 35 minutes. In yet further embodiments, the free radical initiator is DMPA added at an amount of between about 0.01 mol % and about 5 mol % and irradiated with UV light for a duration of between about 10 minutes to about 40 minutes. In other embodiments, the free radical initiator is DMPA added at an amount of between about 0.01 mol % and about 5 mol %, irradiated with UV light having a wavelength of about 365 nm for a duration of about 30 minutes.

In certain embodiments, the catalyst, the free radical initiator, or a combination thereof, may be added to the reaction of the multifunctional thiol compound and the LiTFSI-monomer at the step of dissolving the multifunctional thiol compound in the first solvent, dissolving the LiTFSI-monomer in the second solvent, both at the steps of dissolving the multifunctional thiol compound in the first solvent and dissolving the LiTFSI-monomer in the second solvent, or at the step of dissolving the multifunctional thiol compound and the LiTFSI-monomer together in a solvent. In some embodiments, the free radical initiator is added at the step of dissolving the multifunctional thiol compound and the LiTFSI-monomer together in a solvent.

Advantageously, the methods of the present technology yield a product which can be easily purified and isolated. Therefore, in certain embodiments, the methods of the present technology further comprise precipitating the multifunctional thiol conductor compound. In some embodiments, precipitation of the multifunctionalized thiol conductor compound is performed in dichloromethane (DCM), hexane, pentane, cyclohexane, octane, or dietheyl ether. In other embodiments, precipitation of the multifunctionalized thiol conductor compound is performed in DCM. Advantageously, the multifunctional thiol compound used in the methods of the present technology is soluble in such solvents, thereby allowing for the excess multifunctional thiol compound to be substantially removed in the precipitating step.

In certain embodiments, the mass yield of the multifunctionalized thiol conductor compound obtained by the methods of the present technology is between about 50% and about 99%, between about 60% and about 80%, between about 60% and about 70%, or about 65%.

Figure 2:
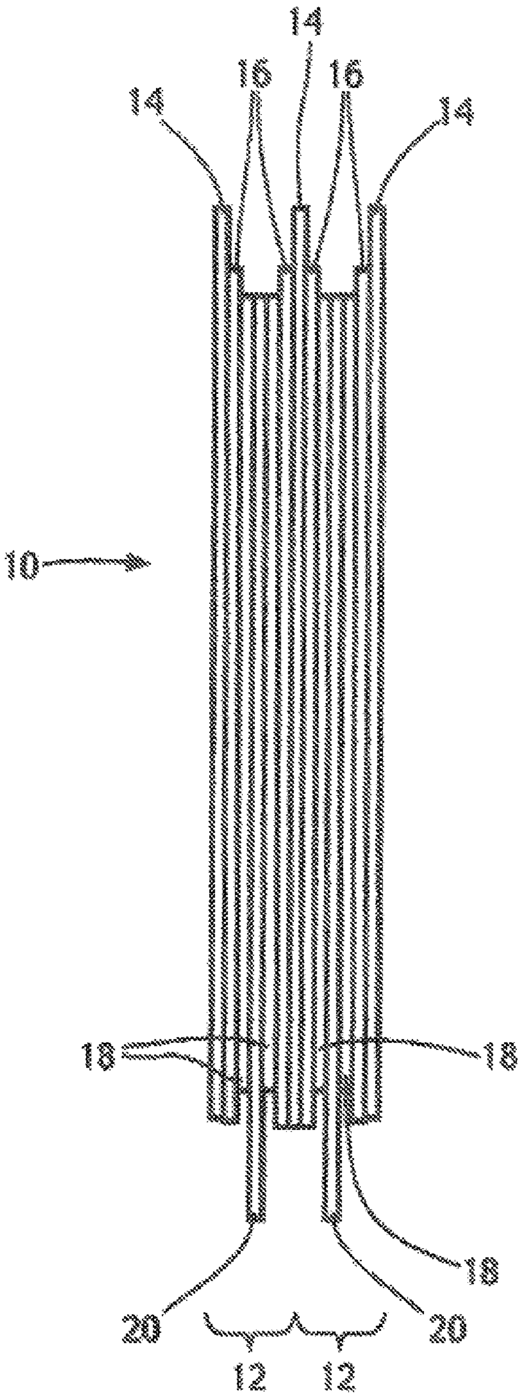
FIG. 2 is a schematic representation of a plurality of electrochemical cells forming a solid-state battery comprising the single-ion conducting polymer electrolytes of the present technology.

From another aspect, the present technology relates to solid-state batteries having a plurality of electrochemical cells, each electrochemical cell comprising a positive electrode, a negative electrode, and an electrolyte layer disposed therebetween. FIG. 2 schematically illustrates a solid-state battery 10 having a plurality of electrochemical cells 12 each including an anode or negative electrode film 14, a solid electrolyte 16, and a cathode or positive electrode film 18 layered onto a current collector 20. The solid electrolyte 16 typically includes a lithium salt to provide ionic conduction between the anode 14 and the cathode 18. In certain embodiments, the anode film 14 is made of a sheet of metallic lithium having a thickness ranging from about 20 microns to about 100 microns. In other embodiments, the solid electrolyte 16 has a thickness ranging from about 5 microns to about 50 microns. In further embodiments, the positive electrode film 18 has a thickness ranging from about 20 microns to about 100 microns. The multifunctionalized thiol conductor compound of the present technology may be integrated in the anode film 14, the solid electrolyte 16 or the cathode film 18.

In certain embodiments, the lithium salt included in the solid electrolyte 16 may be $LiCF_3SO_3$, $LiB(C_2O_4)_2$, $LiN(CF_3SO_2)_2$, $LiN(FSO_2)_2$, $LiC(CF_3SO_2)_3$, $LiC(CH_3)(CF_3SO_2)_2$, $LiCH(CF_3SO_2)_2$, $LiCH_2(CF_3SO_2)$, $LiC_2F_5SO_3$, $LiN(C_2F_5SO_2)_2$, $LiN(CF_3SO_2)$, $LiB(CF_3SO_2)_2$, $LiPF_6$, $LiSbF_6$, $LiClO_4$, LiSCN, $LiAsF_6$, or $LiBF_4$.

The internal operating temperature of the battery 10 in the electrochemical cells 12 is typically between about 40° C. and about 100° C. Lithium polymer batteries preferably include an internal heating system to bring the electrochemical cells 12 to their optimal operating temperature. The battery 10 may be used indoors or outdoors in a wide temperature range (between about −40° C. to about +70° C.).

EXAMPLES

The examples below are given to illustrate the practice of various embodiments of the present disclosure. They are not intended to limit or define the entire scope of this disclosure.

Example 1: Synthesis of a Multifunctionalized Thiol Conductor Compound According to One Embodiment of the Present Technology Pentaerythritol tetrakis(3-mercaptopropionate) (Sigma-Aldrich, 95%, 0.49 g, 1.0 mmol), lithium 1-[3-(acryloyloxy)-propylsulfonyl]-1-(trifluoromethylsulfonyl)imide (Formula VII, 1.0 g, 3.0 mmol) and 2,2-Dimethoxy-2-phenylacetophenone (DMPA, 3 mg, 0.01 mmol) were mixed and dissolved in 3 mL anhydrous THF. The solution was purged with Ar for 20 mins and irradiated with 365 nm UV light (VWR hand lamp) for 35 mins. After the reaction, the solution was precipitated into 20 mL DCM to remove unreacted starting materials. The viscous clear precipitate was collected and vac-dried at 60° C. for about 20 hours and 0.96 g clear hard solid product was obtained. (64% yield). The content and purity of the final product was verified by $^1H$ NMR integration ((DMSO-d6, ppm): 1.97 ($—CH_2—CH_2—SO_2—$, p), 2.42(—SH, m), 2.57-2.74 ($—(CH_2)_2—S—(CH_2)_2—$, m), 3.02($—CH_2—SO_2—$, t), 4.03-4.17 ($—COO—CH_2—CH_2—CH_2—SO_2—$ and $C—(CH_2COO)_4—$, m)).

The synthetic route for the preparation of the multifunctionalized thiol conductor compound according to this embodiment is represented below:

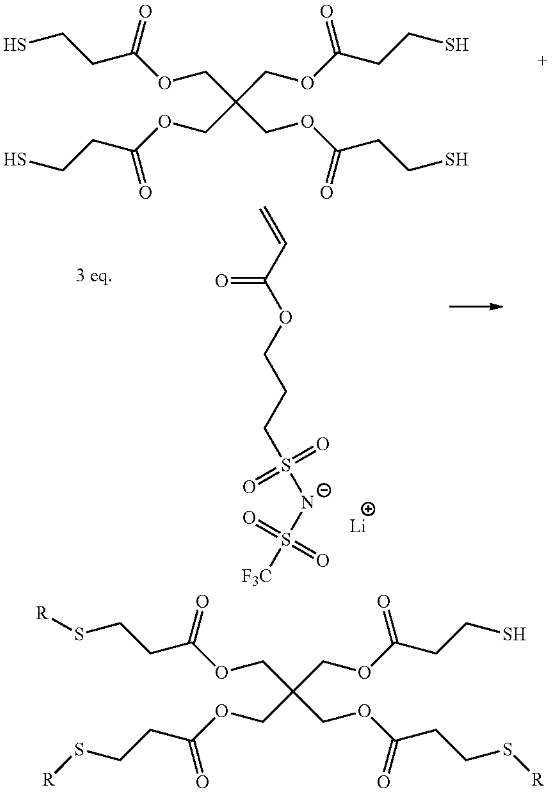

-continued

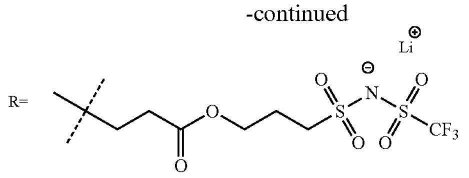

Example 2: Synthesis of a Multifunctionalized Thiol Conductor Compound According to Another Embodiment of the Present Technology The synthetic route for the preparation of the multifunctionalized thiol conductor compound according to this embodiment is represented below:

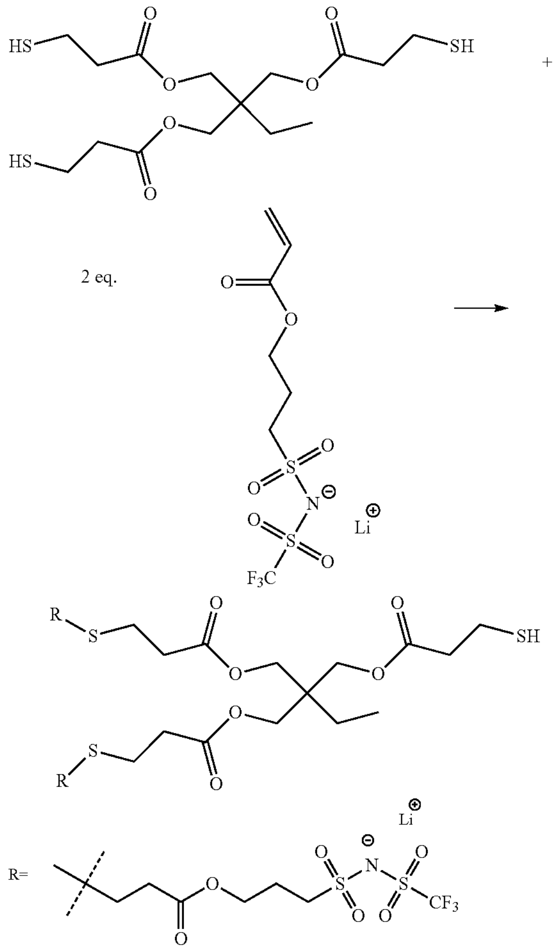

Variations and modifications will occur to those of skill in the art after reviewing this disclosure. The disclosed features may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented. Examples of changes, substitutions, and alterations are ascertainable by one skilled in the art and could be made without departing from the scope of the information disclosed herein.

It should be appreciated that the present technology is not limited to the particular embodiments described and illustrated herein but includes all modifications and variations falling within the scope of the present technology as defined in the appended claims.

All references cited in this specification, and their references, are incorporated by reference herein in their entirety where appropriate for teachings of additional or alternative details, features, and/or technical background.

What is claimed is:

1. A multifunctionalized thiol conductor compound having formula I:

(formula I)

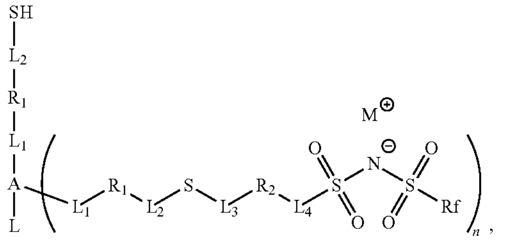

wherein:

A is a substitutable core;

L is absent or present and when present is an alkyl group, a fluorinated alkyl group, a branched alkyl group, an ethylene oxide group, a fluorinated ethylene oxide group, a cycloalkyl group, a fluorinated cycloalkyl group, a phenyl group, or a fluorinated phenyl group;

$R_f$ is F, $CF_3$, $CF_2CF_3$, $(CH_2)_NCF_3$ wherein N is >1, $C_6F_5$, a branched $C_3$-$C_4$ fluoroalkyl group, $-(CF_2CF_2O)_m-CF_2CF_3$ wherein m=1, 2 or 3, $-(CF_2O)$ p/$(CF_2CF_2O)$ q-$CF_2CF_3$ wherein $1 \leq p \leq 10$, $13q \leq 10$, and the $(CF_2O)$ and $(CF_2CF_2O)$ units are randomly copolymerized, or an aryl substituted with at least one fluorine, and at least one electron-withdrawing group;

$M^+$ is a monovalent cation;

$L_1$ are each independently absent or present and when present are each independently an alkyl group, a fluorinated alkyl group, a branched alkyl group, an ethylene oxide group, a fluorinated ethylene oxide group, a cycloalkyl group, a fluorinated cycloalkyl group, a phenyl group, or a fluorinated phenyl group;

$L_2$ are each independently absent or present and when present are each independently an alkyl group, a fluorinated alkyl group, a branched alkyl group, an ethylene oxide group, a fluorinated ethylene oxide group, a cycloalkyl group, a fluorinated cycloalkyl group, a phenyl group, or a fluorinated phenyl group;

$L_3$ are each independently absent or present and when present are each independently an alkyl group, a fluorinated alkyl group, a branched alkyl group, an ethylene oxide group, a fluorinated ethylene oxide group, a cycloalkyl group, a fluorinated cycloalkyl group, a phenyl group, or a fluorinated phenyl group;

$L_4$ are each independently absent or present and when present are each independently an alkyl group, a fluorinated alkyl group, a branched alkyl group;

$R_1$ are each independently absent or present and when present are each independently an ether, a thioether, an ester, an amide, a carbamic acid derivative, urea, a secondary amine, or a tertiary amine;

$R_2$ are each independently absent or present and when present are each independently an ether, a thioether, an ester, an amide, a carbamic acid derivative, urea, a secondary amine, or a tertiary amine; and n>1.

2. The multifunctionalized thiol conductor compound of claim 1, wherein A is a boron atom, an aluminum atom, a carbon atom, or a silicon atom.

3. The multifunctionalized thiol conductor compound of claim 1, wherein A is:

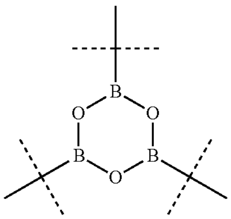
,
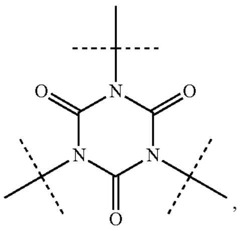
, or
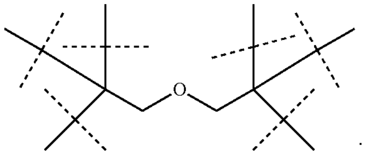
.

4. The multifunctionalized thiol conductor compound of claim 1, wherein n is 2, 3 or 5.

5. The multifunctionalized thiol conductor compound of claim 1, wherein L is an alkyl group.

6. The multifunctionalized thiol conductor compound of claim 5, wherein L is —$CH_2CH_3$.

7. The multifunctionalized thiol conductor compound of claim 1, wherein $R_f$ is $CF_3$.

8. The multifunctionalized thiol conductor compound of claim 1, wherein the electron-withdrawing group is —CN, —$NO_2$, —$CF_3$, or —$SO_2CF_3$.

9. The multifunctionalized thiol conductor compound of claim 1, wherein the monovalent cation is an alkali metal cation.

10. The multifunctionalized thiol conductor compound of claim 9, wherein the alkali metal cation is $H^+$, $K^+$, $Na^+$, $Li^+$, $Rb^+$, or $Cs^+$.

11. The multifunctionalized thiol conductor compound of claim 1, wherein $L_1$ are an alkyl group is a n alkyl group and n is 1, 2, 3, 4, 5 or 6.

12. The multifunctionalized thiol conductor compound of claim 11, wherein $L_1$ are —$CH_2$—.

13. The multifunctionalized thiol conductor compound of claim 1, wherein $R_1$ are an ester.

14. The multifunctionalized thiol conductor compound of claim 1, wherein $L_3$ are an alkyl group.

15. The multifunctionalized thiol conductor compound of claim 14, wherein $L_3$ are $(CH_2)_2$.

16. The multifunctionalized thiol conductor compound of claim 1, wherein $R_2$ are an ester.

17. The multifunctionalized thiol conductor compound of claim 1, having formula II:

(formula II)

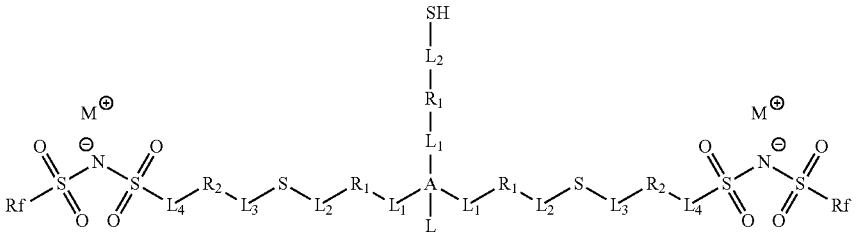

wherein A is a boron atom, an aluminum atom,
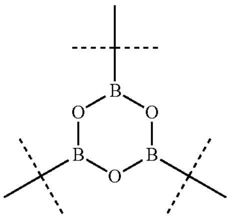
, or
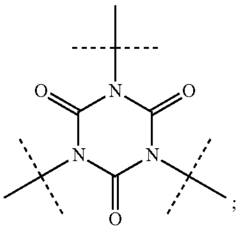
;
L is absent.
18. The multifunctionalized thiol conductor compound of claim 1, having formula II:
(formula II)
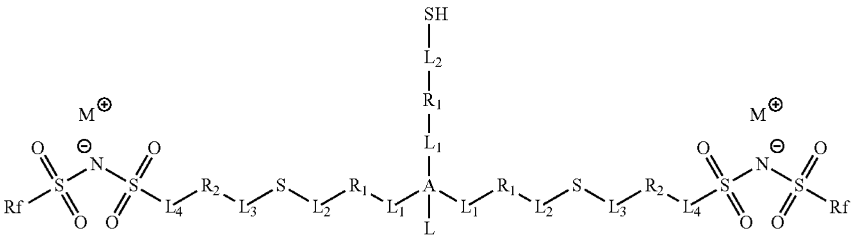
wherein A is a carbon atom or a silicon atom; and
L is present.
19. The multifunctionalized thiol conductor compound of claim 1, having formula III:
(formula III)
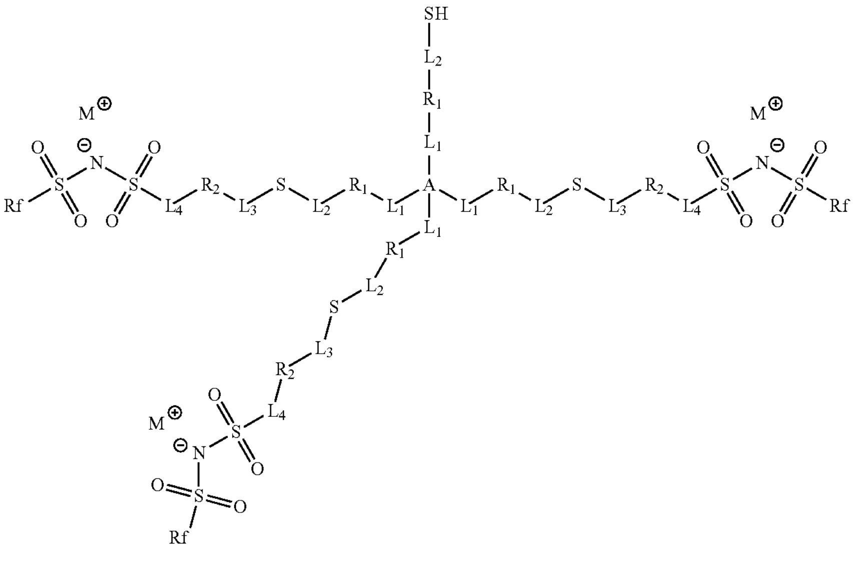
wherein A is a carbon atom or a silicon atom; and
L is absent.

20. The multifunctionalized thiol conductor compound of claim 1, having formula IV:

(formula IV)

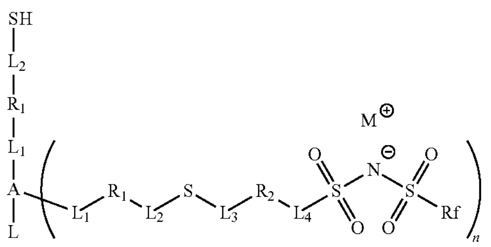

wherein A is a dipentaerythritol core

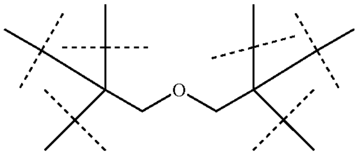

;

L is absent; and n=5.

21. The multifunctionalized thiol conductor compound of claim 1, having formula V or formula VI:

(formula V)

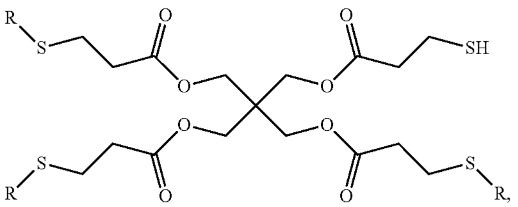

or

-continued (formula VI)

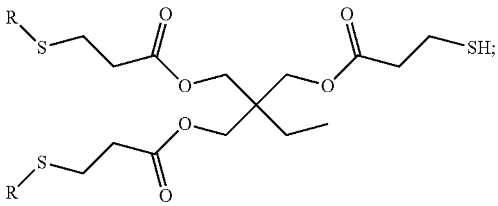

wherein R is

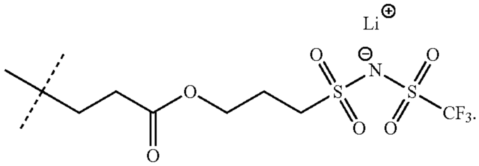

22. A method for the synthesis of the multifunctionalized thiol conductor compound of claim 1, the method comprising reacting a multifunctional thiol compound with a lithium bis(trifluoromethanesulfonyl)imide (LiTFSI)-monomer having a C=C in its backbone.

23. A single-ion conducting polymer electrolyte comprising the multifunctionalized thiol conductor compound as defined in claim 1.

* * * * *